United States Patent
Fitzpatrick

(10) Patent No.: US 10,179,926 B2
(45) Date of Patent: Jan. 15, 2019

(54) MEMBRANE COMPOSITIONS FOR ESTIMATING SOIL MICROBIAL LOAD

(71) Applicant: Prolific Earth Sciences Corporation, Englewood, NJ (US)

(72) Inventor: Judith Fitzpatrick, Englewood, NJ (US)

(73) Assignee: Prolific Earth Sciences Corporation, Englewood, NJ (US)

( * ) Notice: Subject to any disclaimer, the term of this patent is extended or adjusted under 35 U.S.C. 154(b) by 98 days.

(21) Appl. No.: 15/226,214

(22) Filed: Aug. 2, 2016

(65) Prior Publication Data

US 2018/0037926 A1   Feb. 8, 2018

(51) Int. Cl.
  *C12Q 1/06* (2006.01)
  *C12Q 1/04* (2006.01)
  *C12Q 1/24* (2006.01)

(52) U.S. Cl.
  CPC .......... *C12Q 1/06* (2013.01); *C12Q 1/04* (2013.01); *C12Q 1/24* (2013.01)

(58) Field of Classification Search
  CPC .......... A61B 17/3421; A61B 17/3439; A61B 1/0008; A61B 1/00135; A61B 1/00142; A61B 1/00154; A61B 1/126; A61B 1/3132; A61B 2017/3441; A61B 2017/346; A61B 2090/701; A61B 90/70; C12Q 1/06; C12Q 1/04; C12Q 1/24; C12M 33/04; G01N 1/08; G01N 1/14; G01N 2001/1427; G01N 35/1079
  See application file for complete search history.

(56) References Cited

U.S. PATENT DOCUMENTS

| | | |
|---|---|---|
| 3,171,801 A | 3/1965 | Rice |
| 9,315,849 B2 | 4/2016 | Fitzpatrick |

OTHER PUBLICATIONS

Bakken, "Separation and purification of bacteria from soil", Appl Enviro Microbiol., 49(6):1482-7 (1985).
Bending, et al., "Microbial and biochemical soil quality indicators and their potential for differentiating areas under contrasting agricultural management regimes", Soil Biol. BioChem., 36:1785-92 (2004).
Brinton and Haney, "Solvita® Co-2burst respiration: a rapid means to gauge soil biological activity and potentially mineralizable nitrogen", https://solvita.com/wp-content/uploads/2013/11/ISSPA2013_solvita_web2,1 page (2013).
Brinton, "Compost Quality in America", Compost Quality Standards & Guidelines Report, Woods End Research Laboratory, Inc. (2000).
Brinton, et al., "Compost sampling for nutrient and quality parameters: variability of sampler, timing and pile depth", Compost Sci Utilization., 20(3):141-9 (2012).
Czaczyk, et al., "Changes in cell number and the ATP content during the composting process", Polish J Enviro Studies, 10(3):149-53 (2001).
Doran, "Soil health and sustainability: managing the biotic component of soil quality", Applied Soil Ecology, 15:3-11 (2000).
Dreyer and Gardner, "A general method of estimating the relative turbidity or opacity of fluid suspensions including bacterial emulsions", Biochem. J.,10(3):399-407 (1916).
Egamberdiyeva, "The effect of plant growth promoting bacteria on growth and nutrient uptake of maize in two different soils", Applied Soil Ecology, 36:184-9 (2007).
Ekelund, et al., "Distribution with depth of protozoa, bacteria and fungi in soil profiles from three Danish forest sites", Soil Biol Biochem., 33:475-81 (2001).
Fredslund, et al., "Development and application of a most-probable-number-PCR assay to quantify flagellate populations in soil samples", Applied and Enviro Microbiol., 67 (4):1613-8 (2001).
Gans, et al., "Computational improvements reveal great bacterial diversity and high metal toxicity in soil.", Science, 309:1387-90 (2005).
Garrcia-Gil, et al., "Long term effects of municipal solid waste compost application on soil enzyme activities and microbial biomass", Soil Biol. Biochem., 32:1907-13 (2000).
Haney and Haney, "Simple and rapid laboratory method for rewetting dry soil for incubations", Comm Soil Sci Plant Analysis, 41:1493-1501 (2010).
Haney, "Haney/Soil health test information", http://www.wardlab.com/haney_info.aspx, 3 pages (2016).
Haney, et al., "Effect of roundup ultra om microbial activity amd biomass from selectrd soils", J Environ Qual., 31:730-5 (2002).
Haney, et al., "Soil carbon and nitrogen mineralization: influence of drying temperature", Soil Sci Soc Am J., 68:489-92 (2004).
Hill, et al., "Methods for assessing the composition and diversity of soil microbial communities", Applied Soil Ecology, 15:25-36 (2000).
Holmes and Zak, Soil microbial biomass dynamics and net nitrogen mineralization in northern hardwood ecosystms, Soil Sci Soc Am J., 58:238-43 (1994).
Hoorman and Islam, "Understanding soil microbes and nutrient recycling", Fact Sheet, Ohio State University, (2010).
Ingham, et al., "Interactions of bacteria, fungi, and their nematode grazers: effects on nutrient cycling and plant growth", Ecological Monographs, 55 (1):119-40 (1985).

(Continued)

*Primary Examiner* — Deborah K Ware
(74) *Attorney, Agent, or Firm* — Pabst Patent Group LLP

(57) ABSTRACT

Devices, methods, and kits for easy, accurate, and fast estimation of soil microbial load are provided. The devices include membranes that are rapidly wettable with aqueous fluids and retain soil microorganisms of up to 200 micrometers in size, without retaining soil pigments. The method requires reconstituting a soil sample in an extraction fluid so that the microorganisms in the soil sample are released from particles of the soil sample and into the extraction fluid. The method does not require a filtration step. The extraction fluid containing the microorganisms suspended therein is then pipetted onto the membrane device, or the membrane is dipped into the extraction fluid. The color appearing on the membrane is then compared to color intensity gray scale strips to determine the soil microbial load.

24 Claims, 5 Drawing Sheets

(56) References Cited

OTHER PUBLICATIONS

Insam, et al., "Relationship of soil microbial biomass and activity with fertilization practice and crop yield of three ultisols", Soil Bid Biochem., 23(5):459-61 (1991).
Leckie, et al., "Comparison of chloroform fumigation-extraction, phospholipid fatty acid, and DNA methods to determine microbial biomass in forest humus", Soil Biol Biochem., 36:529-32 (2004).
Lorian and Gray, "Separan NP10, a viscosity-producing substance in culture media", Appl Microbiol., 14(5):836 (1966).
Lugtenberg, et al., "Microbe-plant interactions: principles and mechanisms", Antonie van Leeuwenhoek, 81:373-83 (2002).
Malhotra, et al., "Nutrient removal from secondary effluent by alum flocculation and lime precipitation", Int J Air Wat Poll., 8:487-500 (1964).
Martens, "Current methods for measuring microbial biomass C in soil: potentials and limitations", Biology Fertility of Soils, 19(2-3):87-99 (1995).
Martin and Brathwaite, "Compost and compost tea: principles and prospects as substrates and soil-borne disease management strategies in soil-less vegetable production", Biological Agriculture Horticulture, 28(1):1-33 (2012).
Mestre, "A precision photometer for the study of suspensions of bacteria and other microorganisms", J Bacteriology, 30(4):335-58 (1935).
Nel, et al., "A turbidimeter for measuring soil-particle concentration in suspensions", S Afr Tydskr Plant Grond,4(2):90-3 (1987).
Portillo, et al., "Cell size distributioms of soil bacterial and archaral tavxa", Appl Envir Microbiol., 79(24):7610-7 (2013).
Roesch, et al., "Pyrosequencing enumerates and contrasts soil microbial diversity" ISME J., 1:283-90 (2007).
Schloss and Handelsman, "Toward a census of bacteria in soil", PLoS Comput Biol., 2(7):e92. (2006).
Shrestha, et al., "Microbially enhanced compost extract: does it increase solubilisation of minerals and mineralization of organic matter and thus improve plant nutrition", Bioremediation and Biodegradation, 3(5):1-9 (2012).
Suzuki, et al., "DAPI direct counting underestimates bacterial abundances and average cell size compared to AO direct counting", Am Soc Limnology Oceanography, 38 (7):1566-70 (1993).
Torsvik, et al., "High diversity in DNA of soil bacteria", Appl. Enviro. Microbiol., 56(3):782-7 (1990).
Turner, et al., "Rapid estimation if microbial biomass in grassland soils by ultra-violet absorbance", Soil Biol Biochem., 33:913-9 (2001).
Valpassos, et al., "Effects of soil management systems on soil microbial activity, bulk density and chemical properties", Pesquisa Agropecuaria Brasileira, 36(12):1539-45 (2001).
Van Veen and Paul, "Conversion of biovolume measurements of soil organisms, growth under various moisture tensions, to biomass and their nutrient content", Applied and Enviro Microbiology, 37(4):686-92 (1979).
Van Veen, et al., "Fate and activity of microorganisms introduced into soil", Microbiol Molecular Biology Rev., 61(2):121-35 (1997).
Waste Water, "Wastewater treatment systems augmenting handbook operation and maintenance", Unified Facilities Criteria (UFC), pp. 1-126 Jan. 16, 2004.
West and Sparling, "Modifications to the substrate-induced respiration method to permit measurement of ,microbial biomass in soils of differing water contents", J Microbiol Meth., 5:177-89 (1986).
Wilson, "Water quality notes: water clarity (tubidity, suspended solids, and color)", Univ FI IFAS extension, 2010.
Witt, et al., "A rapid chloroform-fumigation extraction method for measuring soil microbial biomass carbon and nitrogen in flooded rice soils", Biol. Fertility Soils, 30(5-6):510-9 (2000).
Zajic and LeDuy, "Flocculant and chemical properties of a polysaccharide from pullularia pullulans", Appl Microbiol., 25(4):628-35 (1973).

MEMBRANE COMPOSITIONS FOR ESTIMATING SOIL MICROBIAL LOAD

STATEMENT OF FEDERALLY SPONSORED RESEARCH

None.

FIELD OF THE INVENTION

The invention is generally directed to methods and devices for easy and fast colorimetric estimation of a soil microbial load. without the requirement for spectrophotometers, turbidity detectors, or sample filtration.

BACKGROUND OF THE INVENTION

Measurement of microbial biomass or other soil analytes is difficult because of the large amount of particulate matter that is irrelevant to the measurement of these analytes and because the color of an extract may preclude assaying for analytes by methods such as spectrophotometery, turbidity, nephalometry and visual comparison. One of the most difficult parameters to measure is Microbial Biomass which is an excellent indicator of soil and compost quality and is a predictor of soil fertility. Soil microbes recycle the organic matter in soil and convert it into forms that can be utilized by plants. Bacteria represent the most numerous of the microbial life in soil and serve as the bottom rung of the microbial soil food chain which consists of bacteria, fungi, protozoa, algae and nematodes. Abundant microbial life indicates that the nutrient levels of soil are sufficient and balanced and that there is an absence of significant levels of deleterious or poisonous substances such as heavy metals or high concentrations of salts.

Studies have revealed that microbial biomass is a predictor of soil fecundity and correlates highly with other predictors of fecundity such as organic carbon and soluble organic carbon and crop yield. However, tests and test standardization to establish the microbial content of soils are not extensively utilized in large part due to the fact that existing methods are laboratory tests and carry a high cost or have poor performance.

Currently, several laboratories provide commercial in-house services to estimate the numbers of various different types of microbes in soil. These estimates are based upon laboratory tests that are costly, labor intensive and results are not available for 7-21 days. Because less than 10% of soil microbes can be cultured and then only with great difficulty and time, analyses may be performed by direct counting using a microscope and a diluted sample on a slide. The slide can be difficult to read because microbes are attached to the soil particles, and expertise is required to distinguish between bacteria, fungi and protozoa, rendering these tests prohibitively expensive for use as routine quality control. In addition, soil samples must be transported to the laboratory for analysis during which time it has been shown that microbial biomass can rapidly decline, and it can take days or weeks for the results to be reported. These methods are not practical for estimation of the microbial content of composts and compost extracts, which must be used within one or two days of formulation. Further, the results are not consistent from lab to lab, due to the subjective nature of visual counts. Analytical methods of microbial biomass, such as phospholipid fatty acid analysis (PLFA) and carbon fumigation cost upwards of $80: PLFA calculates the weight of the various phospholipids of microbes which is very useful in indicating the microbial composition as different phospholipids are associated with certain species. Microbial biomass can be back calculated from the total weight of phospholipids using a factor of about 100. This method has been shown to have about a 70% correlation with the carbon fumigation method, which is the gold standard for estimation of microbial biomass. The carbon fumigation method costs about $500 and is provided by only a few U.S. labs. It measures the amount of carbon dioxide produced by actively metabolizing microbes over a set period of time, usually a week: This test is done is quadruplicate as there is enough variation in one sample that only an average is considered accurate. Microbial biomass is back calculated from this using a factor. Both of these methods do not measure biomass but infer it from microbial parameters, thus there is not excellent correlation from method to method. For the microbial count, PLFA and carbon fumigation methods there is so much lab to lab variation that one cannot compare results from one lab to those of another, although each lab's method appears rather reproducible. The lab to lab variability of these methods is due to the fact that they are complex procedures performed slightly differently from lab to lab, they are technique dependent and the microbial biomass measured is undoubted heavily influenced by the various preparation procedures that are used. These procedures affect the microbes which are living creatures. The carbon burst method measures $CO_2$ generation by microbial metabolism over a 24 hour or longer period. It utilizes a dried sample. It is well known that drying kills metabolically active and dividing microbes which is the case during periods of plant growth. Thus it measures the microbial activity of the least metabolically active microbes. It can also be used to measure anaerobic respiration in a tight container.

Bacteria are typically the most abundant and diverse microbial component of soil. A standard laboratory technique for quantitation of bacteria is based upon spectrophotometric measurement of turbidity within a solution. However, this method is problematic for measurement of the bacterial content of soil samples because the particles and pigments in soil also contribute to turbidity, reflectance and/or transmittance measurements. In addition, many microbes in soil are firmly attached to the soil particles and do not readily go into solution. Further, it is not practical to apply these methods to a field test to assess microbial biomass in soil because of the need for a turbidometer or spectrophotometer, which precludes efficient use in the field. In order to be of most use to agriculturists, low cost accurate estimates of microbial numbers are required on-site and within minutes to hours of sampling, e.g. to determine whether a new treatment increased microbial growth, how much to dilute a compost extract, or whether further fertilizer treatments are necessary.

The device described in U.S. Pat. No. 9,315,849, is useful in a method for separating bacteria from soil particles and estimating bacterial biomass by turbidity. In contrast, it would be preferable to have a method which optimizes the extraction procedure to allow the extraction of both bacteria and protozoa. The extracted microbes are colored. The intensity of the color correlates with the microbial biomass, allowing microbial biomass to be estimated from the intensity of the color, estimated from spectrophotometry or by visual methods.

There remains a need for easy, accurate, and fast estimation of soil microbial load that does not require laboratory instrumentation and can be practiced in a field setting, because microbial biomass is the single best predictor of soil quality.

Therefore, it is the object of the present invention to provide a method and devices for easy, accurate, and fast estimation of soil microbial load.

It is another object of the present invention to provide methods for easy, accurate, and fast estimation of soil microbial load.

It is yet another object of the present invention to provide kits for easy, accurate, and fast estimation of soil microbial load.

SUMMARY OF THE INVENTION

Devices, methods, and kits have been developed for easy, fast, and accurate measurement of soil microbial load. The devices include an extraction solution containing a high concentration of salt and detergent, a whisking procedure vigorous enough to dislodge microbes from soil but mild enough to not disrupt the microbe or pulverize the soil particles, and a fluid-absorbable membrane wettable by a fluid, such as an extracted soil sample, within about 5 seconds to 30 seconds after applying the extracted soil sample. Preferably, the fluid-absorbable membrane is wettable within 0.1 sec to 2 sec by the extracted soil sample. The device membranes do not bind any components of the extracted soil sample except the extracted soil sample microbes but the pore size should retain microbial biomass on the surface. Typically, the membrane has a pore size capable of retaining the extracted microbes on its surface and absorbing the extraction solution and any solubilized soil pigments. The exposed membrane turns color due to the pigments in the microbes: these pigments are composed of microbe internalized soil pigments and other microbial pigments, e.g. fungal spores appear almost black.

The devices may also be in a package form. In this aspect, the fluid-absorbable membranes are sandwiched between two or more adhesive-coated sheets which includes a sample window. The package may also include a quality control window. The packages and membranes described herein may be placed in a plastic wrap or a pouch and/or have a label attached.

Typically, the extraction process, removes 95% of the soil particles from the extraction fluid and the surface of the membrane sample window retains the extracted soil sample microbes having a size of between about 1 micrometer and 200 micrometers, but does not retain any other component of the extracted soil sample. By surface is meant that area of the surface of the membrane which is visible and displays the colored microbes. Other components of the extracted soil sample include pigments and particulate organic or inorganic solids that are smaller than 1 um and which migrate into the membrane in diluted form.

The devices can be precut to any shape. An exemplary device may be a square with 2.5 cm sides, and a depth of between 0.1 mm and 5 mm.

The membrane of the devices may be formed of natural or synthetic polymeric membranes, or combinations thereof. Exemplary polymers for forming the membrane include, but are not limited to, fiberglass, anopore (ANP), cellulose acetate (CA), cellulose nitrate (CN, nitrocellulose), nylon/polyamide (NYL), polycarbonate (PC), polyethersulfone (PES), polypropylene (PP), and regenerated cellulose (RC). Exemplary fiberglass membranes include fiberglass prefilter material such as that sold by Diagnostic Sciences Corporation or Laboratory Instrumentation Services or WHATMAN® glass microfiber filters of the following grades: 934-AH®, GF/A, GF/B, GF/C, GF/D, GF/F, GMF, GF, with or without non-interfering binders Also described are methods for easy, fast, and accurate measurement of soil microbial load. An exemplary method includes applying an extracted soil sample to the device and detecting the microbial load by color intensity. Since different soils have different pigments that also color the microbes in that soil, the differences in color are corrected by reading with a gray scale strip, such as is commonly used for evaluating color intensity in sewing crafts. Generally, the grey scale comparator is placed next the color to be graded and the observer wears red tinted glasses. This has been modified by placing transparent red filter material on the top of the grey scale so that the window for viewing the sample along with the grey scale sample are covered with the red film.

Generally, the method includes obtaining a soil sample containing microorganisms; preparing an extracted soil sample by applying an extraction fluid to the soil sample, whisking to extract and extracting the microorganisms into the extraction fluid; allowing the whisked soil sample to settle (soil particles settle out during this process); applying several drops of the top cm of the extracted soil sample onto the device; depositing color on the device: obtaining the microbial load by comparing the shade of the developed color with colors present on the gray scale strip. For example, whisking of the extraction fluid with the soil sample may not be required prior to letting the extracted soil sample settle, i.e. shaking may be sufficient for liquid samples, although it is always required for compost and soil extracts. The extraction fluid typically includes releasing agents, such as sodium chloride, calcium chloride, and a polysorbate-type nonionic surfactant formed by the ethoxylation of sorbitan before the addition of lauric acid, such as TWEEN® 20. The extraction fluid may also include clarifying agents, anti-foaming agents and preservatives.

Typically, the gray scale strip reflects at least six soil ratings: e.g. very poor, poor, acceptable, good, very good, excellent. The gray scale strips may be in any form: chart, strip, color discs, or have digital values for the color shades to aid with electronically establishing the soil microbial load.

Also described are kits containing the membrane device, whisking devices, extraction fluid or materials for preparation of extraction fluid, soil sampler, the gray scale strip, pipette for applying sample to membrane and instructions for use. The kits may also provide premeasured releasing agents, an anti-foaming agent, a bleaching agent tablet, a reaction vial, and a pipette for drawing out the extracted soil sample containing suspended microorganisms and a device for sifting the soil to remove root and other debris the sample prior to measuring the soil sample for testing. The kit may also provide shaking or whisking devices.

DETAILED DESCRIPTION OF THE INVENTION

I. Definitions

Figure 1A:
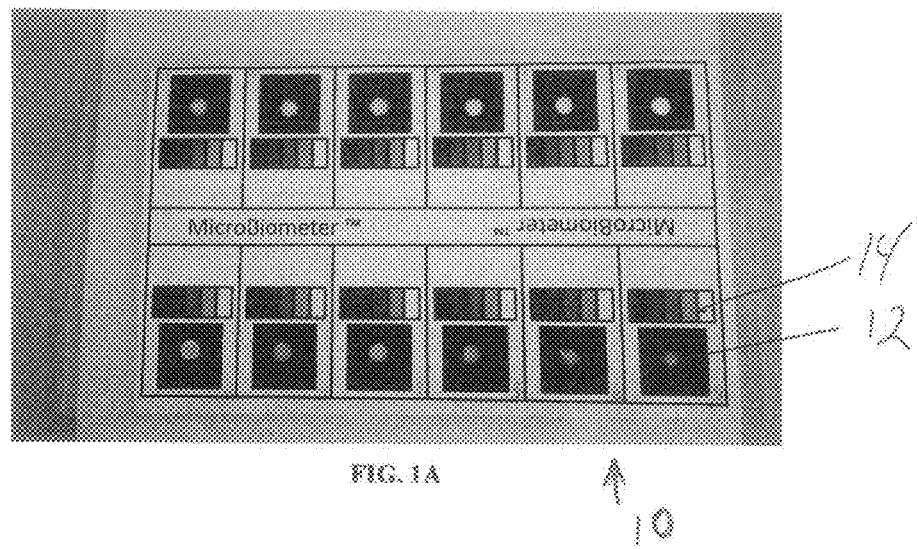
FIG. 1A is an image of the MicroBiometer™, with twelve sample application sites 12 and a gray scale 14 underneath each sample well.

As described herein, "membrane" refers to a pliable sheetlike structure. The membrane is a barrier to microbes. The membranes can be sheets, or sheetlike structures, that can be cut into any geometric shape to any length and width. The thickness of the membrane may vary dependent on the nature of membrane used. The membrane contains pores of a size and distribution that retains microbes on the surface.

The terms "soil" and "soil sample" as used herein, refer to any earthy mix of minerals, air, water, and organic matter. Soils include composts, compost extracts and compost teas and microbial soil amendments. Soil or soil samples may be dry or wet.

"Compost extract" refers to a solution prepared by mixing compost and water and removing most of the solid residual. "Compost tea" refers to a compost extract fortified with other nutrients, such as organic and/or inorganic fertilizer.

The term "microbes" refers to microscopic organisms such as bacteria, fungi, algae and protozoa.

The terms "microbial biomass", "microbial content" and microbial number" refer to the amount of microorganisms in a given habitat. Microbial biomass, content or numbers can be expressed either as the weight of organisms per unit area or as the volume or number of organisms per unit volume of habitat or solution or by indicating a fecundity level such as that indicated by the grey scale.

The terms "extracted soil sample" refers to the extraction fluid containing microorganisms extracted from the soil sample placed therein. The extracted microorganisms are suspended in the extraction fluid of the extracted soil sample. Not all microbes are released during the process described herein. However, the amount released is consistent from test to test and is consistent with microbial biomass estimated by other methods. See correlation with PLFA in Figs x. The extracted organisms as verified by microscopy consist of fungal ribbon stacks, bacteria, amoeba and other protozoa and various spores including fungal spores.

The terms "fluid", "aqueous fluid" refers to a fluid containing between about 75% and 99% water. The water of the aqueous fluid can be stream water, tap water, purified water, filtered water, deionized water, or distilled water.

The term "the field" refers to the location of origin of a sample, such as the geographic location at which a given sample is obtained. Typically, the term refers to a non-laboratory setting.

The term extraction fluid, refers to a solution containing salts and detergents in a concentration optimized to release microbes without destroying them during the time required for assay. The extraction fluid may be provided in liquid form in a tube or as a tablet or powder to be added to water. Extraction fluid may contain preservatives such as sodium azide and or other constituents for quality control.

The term whisking refers to treating the extraction soil solution to mechanical agitation that assists in releasing microbes in extraction fluid from soil particles, but is not so vigorous as to disrupt the microbes or to pulverize soil particles so that they will not precipitate during the settling process, e.g. sonication creates soil particles that remain in extraction fluid during settling. The term colored microbes refers to the color possessed by microbes due to ingested soil particles and microbial pigments.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approximately +/−10%; in other aspects the values may range in value either above or below the stated value in a range of approx. +/−5%; in other aspects the values may range in value either above or below the stated value in a range of approx. +/−2%; in other aspects the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

II. Devices

The devices include membranes, which may be enclosed and/or pretreated membranes, extraction fluid, membranes, and whisking devices, for accurate detection of soil microbial load. In some forms, the membranes are enclosed in a package. The package may include a sample window presented by one or more openings for sample application.

The seal around the sample window restricts movement of microbes past the window. The package may also include a quality control window presented by one or more openings for quality control of the detection process.

The membrane retains the microbes on the surface providing a colored sample and allowing the intensity of the color in the window to be used to estimate microbial biomass, thus it is important that microbes not migrate outside the window perimeters. In a preferred embodiment the membrane is enclosed in heat laminated material. This process insures a secure seal around the window which retains microbes in the window area and at a thickness of about 10 mm (2×5 mm) is sufficiently firm to prevent casual bending that would break the seal around the window. Heat laminating materials such as those provided by Uline contain an adhesive that does not migrate except at high temperatures which is a prerequisite for the device as adhesive that migrates can block the pores of the membrane and inhibit the passage of fluid into the membrane.

The strip device can be utilized in two ways: it can be dipped or have sample applied to the window. If it is dipped the strip has to contain a volume of membrane that will only absorb the desired amount of fluid. Alternatively the strip can have a test window with an indicator such as a color change or disappearance that indicates sufficient fluid has been absorbed. In the case of a dipstick, each test is an individual strip. In the case of a strip to which sample is added, e.g. by pipette, the strip can be a membrane of almost any volume to which a measured amount of sample is added to the window. In this case the membrane can be packaged with one or more windows and/or quality control windows. The laminated strip can have a label on the top that contains instructions for application of sample and indicates window positions. The laminate can be in the form of pouches or rolled film and lamination should be performed according to laminating instructions provided by the laminator and laminating material. The membrane used for the test must be heat resistant so that pore size and structure is not adversely affected by the process. Fiberglass membranes sold as pre-filter material by DSC Data Service Corporation or LIS Laboratory Instrument Services serve well for lamination: they have the correct pore size, they are wettable, they are not adversely affected by lamination and they remain functional for long periods as evidenced by accelerated stability testing at 70 C. For optimal performance the side of the membrane exposed by the window should be as smooth as possible. The DSC membrane has a rough and a smooth side. The windows of the strip can be only on one side of the laminate or on both sides. In a preferred version the window/s is only on one side as this prevents the tester from wetting the strip if it is placed on a wet surface.

Figure 1B:
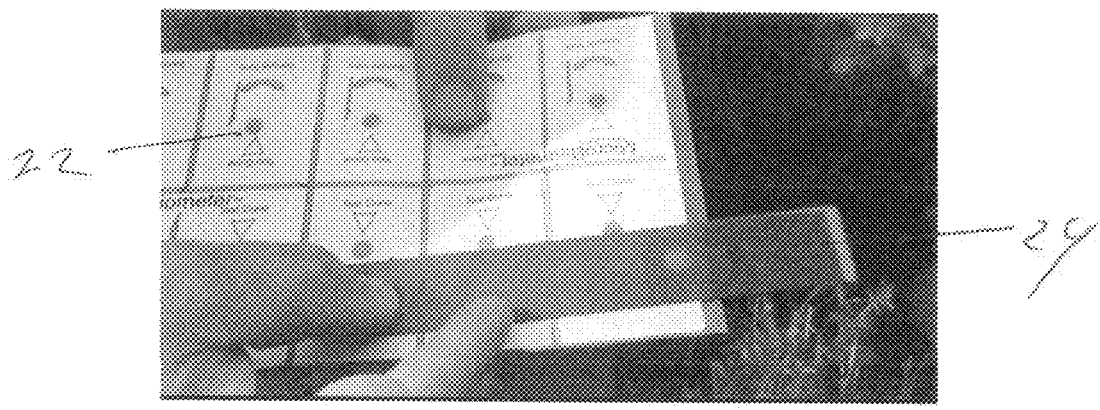
FIG. 1B shows device 20, which sample application site 22, which can be compared to a separate color scale 24 for determination of the concentration.
Figure 1C:
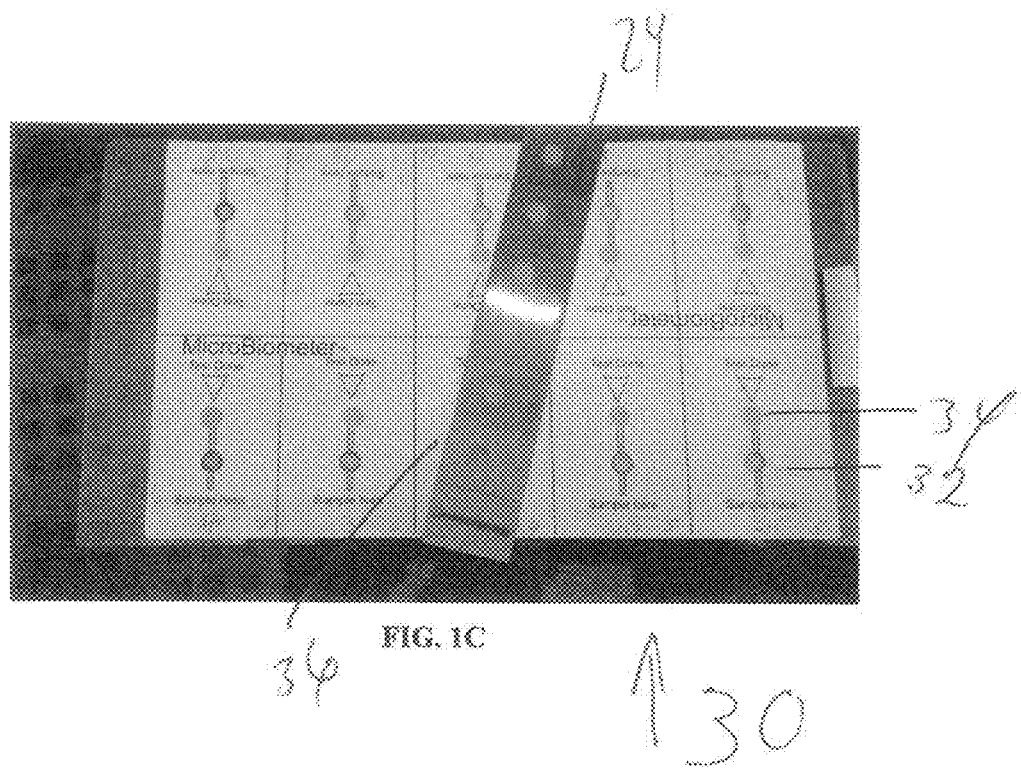
FIG. 1C is a test strip device 30 with sample application site 32, and test done site 34, which is then compared to color analysis scale 24 to determine the concentration of microorganisms in the sample.

Representative devices are shown in FIGS. 1A-1C. The device 10 shown in FIG. 1A includes 12 sample application sites 12, with a grey scale 14 below and adjacent to each site 12, allowing for immediate comparison to the grey scale 14, which is accompanied by a value for each shade for the estimated number of microorganisms in the sample.

FIG. 1B shows device 20, which sample application site 22, which can be compared to a separate color scale 24 for determination of the concentration.

FIG. 1C is a test strip device 30 with sample application site 32, and test done site 34, which is then compared to color analysis scale 24 to determine the concentration of microorganisms in the sample.

A. Membranes

The membrane surface exposed in the window should be as even as possible to provide even distribution of the microbes. Devices described herein include fluid-absorbable membranes. Typically, the devices are sheet-like membranes of any desired geometric shape and dimension. The sheet-like membranes are typically thin membranes that can be cut to a desired width and length. The membranes may be precut to a desired width or length, or can be provided as membrane sheaths for cutting by the end user to the desired geometric shapes and dimensions. For example, the membrane is cut to a 2.5 cm square, but other dimensions are contemplated. The size of the membrane can be adjusted to increase or decrease the amount of fluid it can absorb and thus increase or decrease the level of detection/sensitivity.

In a preferred embodiment the membrane is a fiberglass membrane enclosed in a heat laminated device. Heat lamination materials contain adhesives that only migrate at very elevated temperatures thus insuring that the functionality of the membrane will not be compromised by adhesive seepage over time. Heat laminated devices have the advantage of securely sealing the area around the sample window so that microbes are retained on the surface of the membrane window only. For example, a 10 mm laminating material provides a sturdy support for the membrane a secure seal around the window and very cheap device. The seal around the membrane window must be secure, otherwise microbes will migrate on the surface of the membrane beyond the window and the intensity in the window will be lower than it should be. So far we have five years' stability as ascertained by accelerated stability study at 70° C.

1. Membrane Materials

Membranes are typically made from natural or synthetic polymers. The membranes may also be made of a combination of natural and synthetic polymers. Suitable polymers include fiberglass, anopore (ANP), cellulose acetate (CA), cellulose nitrate (CN, nitrocellulose), nylon/polyamide (NYL), polycarbonate (PC), polyethersulfone (PES), polypropylene (PP), regenerated cellulose (RC. In preferred embodiment, the membrane is fiberglass because it is resistant to the high temperature used in heat lamination is wettable and does not generally bind the pigments in soil.

Examples of suitable fiberglass membranes include DSC and LIS fiberglass prefilter material and WHATMAN® glass microfiber filters of the following grades: 934-AH®, GF/A, GF/B, GF/C, GF/D, GF/F, GMF, GF, and LIS, with or without binders. Binders may be organic or inorganic.

The membranes are fluid-absorbable. Typically, the fluid is an aqueous fluid containing between about 75% and 99% water. For example, the fluid absorbed by the membrane may contain about 60%, 65%, 70%, 75%, 80%, 85%, 90%, and 95% water. The water of the aqueous fluid can be stream water, tap water, purified water, filtered water, deionized water, or distilled water.

Membranes in an aqueous environment have an attractive or repulsive response to water. The material composition of the membrane and its corresponding surface chemistry determine the interaction with water, thus affecting its wettability. Typically, the membranes are made of hydrophilic material. Hydrophilic materials are characterized by the presence of active groups that have the ability to form "hydrogen-bonds" with water. Hydrophobic materials have little or no tendency to adsorb water and water tends to "bead" on their surfaces (i.e. discrete droplets). Hydrophobic materials possess low surface tension values and lack active groups in their surface chemistry for formation of "hydrogen-bonds" with water. The wettability of the membrane can be enhanced by detergent and other substances in the extraction fluid.

Typically, the membranes described herein retain microbes with a size (diameter) between 1-2 um and 200 micrometers, and soil pigments being smaller than 1 um are not retained. These membranes are porous, with a pore diameter of between about 1 micrometer and 10 micrometers. Microorganisms larger than 1-2 micrometers in diameter are not retained on the surface of the membrane by the membrane pores and are passed through the membrane. Typically, the membranes include pore sizes having an average diameter from between 0.5 micrometers and 20 micrometers. For example, the membrane pore size is from between 0.5 micrometers and 10 micrometers.

The membrane is able to absorb sufficient extraction fluid to capture a significant quantity of microbes to stain the sample window. The membrane has a volume that allows absorption/retention of a minimum volume of extracted soil sample with microorganisms suspended therein for accurate determination of the microbial load. Suitable membrane depth is from between 0.1 mm and 10 mm, but preferably is between 0.1 mm and 2 mm. Suitable volumes of extracted soil sample that can be applied to the membrane devices for accurate determination of microbial load of the soil include average volumes of between 100 µl and 1 ml. For example, the volume of extracted soil sample that can be applied to the membrane devices for accurate determination of microbial load of the soil includes volumes of between 50 µl and 1000 µl.

The microbes retained by the membrane provide the change in membrane color, which is then correlated with a given microbial load.

B. Packaging

For example, the membranes are provided in a laminated package. The package may include a sample window through which a sample is applied to the membrane. The size of the sample window together with the applied volume of extracted microbial solution will determine the intensity of color in the window. If the window is larger, a larger volume of fluid will be needed to give the same intensity. Typically, the sample window is ¼ inch or slightly larger so as to facilitate color comparison and cell phone reading. The package may also include a quality control window.

1. Sample and Quality Control Windows

For example, the membrane is enclosed in a self-sealing package with a first set of one or more openings for the sample application (sample window). An optional second set of one or more openings may be present for quality control purpose (quality control window)

The test sample can be applied to the membrane by dipping the membrane into the sample. Alternatively, the test sample may be pipetted onto the membrane at the sample window.

The quality control window may be used to monitor the quality of the assay for the detection of soil microbial load. Any number of quality control functions can be performed by the quality control window opening(s).

The one or more opening(s) of the quality control window may include a color spot (marker) that disappears, changes color, when fluid reaches these one or more quality control openings. This may signal to the user that sufficient test sample (such as an extracted soil sample) has been applied to the sample window. Alternatively, the one or more quality control openings may be free of a color spot. Any pigment in the sample will color these one or more openings and indicate that the result is compromised by pigment in the sample.

In another aspect, the quality control window may display a pigment in the sample that is not associated with microbes. The quality control window displays the soil pigment that uniformly stains the whole membrane and indicates that this intensity should be subtracted from the intensity of the sample window.

2. Window Seals

Typically, the sample window in a package are sealed at their perimeter to prevent sample leakage/spread to areas outside of the sample window.

The seal can be any adhesive coated sheet cut to the size and shape of the package with openings for window(s). For example, the membrane may be positioned between two adhesive coated sheets, with openings present at least on one of the adhesive coated sheet for the window(s). Examples of suitable adhesive coated sheets include ULine laminate and AVERY® ULTRADUTY™ GHS chemical labels, and other permanent or removable labels or. Heat laminates are made from polyester film and extruded heat seal adhesive. Typically, the amount of polyester film and adhesive is described in a ratio. For example, a 10 mil film which is "4/6" is constructed of polyester 4 mils thick and heat seal adhesive which is 6 mils thick. Self sealing laminate may also be used but compatibility of adhesive with the membrane and on-going stability must be demonstrated.

C. Wrap or Pouch

The membranes and packages can be placed inside a plastic wrap or laminating pouch. The plastic wrap or the pouch may include a sample window and/or a quality control window. The plastic wrap or a pouch may be soft, pliable, or hard material. Exemplary materials for the plastic wrap or a pouch include, but are not limited to, polyester, polyethylene, polyethylene-linear low density (LLDPE), polyethylene low density (LDPE), thermoplastic olefin, polyethylene terephthalate, poly(methyl methacrylate) (PMMA).

For example, only one membrane or package may be present in one plastic wrap or a pouch.

III. Methods of Making the Devices

The devices are made by sandwiching a suitable membrane or filter between two or more adhesive coated sheets. One or both of the adhesive coated sheets will include one or more openings for a sample window and/or quality control window. Typically, the membrane is entirely sealed within package except for the windows as this prevents inadvertent wetting at other than the sample site.

An exemplary device is the MicroBiometer™ Strips presented in FIG. 1.

IV. Methods of Using the Devices

The advantages of the method described herein are that the entire microbial biomass including fungi is extracted, thereby providing a more complete picture of the microbial biomass, the absence of a filtration step for soil, and the ability to measure color spectrophotometrically or visually or with a cell phone app as opposed to requiring a laboratory type instrument colorturbidity measurements.

The method for determining the microbial load of a soil requires:

1. a soil sample;
2. A soil sampler capable of delivering a set volume of sample
3. an extraction fluid;
4. agitation devices (optional);
5. pipette (optional); and 6. a membrane device, such as the MicroBiometer™ and 7. color intensity gray scale strip or cell phone app, or a colorimeter.

Generally, the method includes reconstituting the soil sample in the extraction fluid so that the microbial biomass of the soil is released from the soil particles and enters the extraction fluid. The extraction fluid with the extracted microorganisms suspended therein (extracted soil sample) is then pipetted into the sample window of the membrane device, or the membrane is dipped into the extraction fluid. The color appearing in the sample window, or at the tip dipped into the extraction fluid, is then compared to color intensity gray scale strips to determine the soil microbial load.

A. Soil Samples

The soil samples include solid soil, which may be dried or wet soil. Soil samples containing an earthy mix of minerals, air, water, and organic matter can be used. Soil samples can be liquids, such as compost extract or compost tea. Typically, soil samples compose 5-20% of the testing reaction volume.

1. Compost

Composted organic matter and humus is a predominant component of the nutrient content of soil. Because solid compost is heavy and requires spreading for use as a fertilizer, many who use compost as fertilizer prefer to extract the nutrients and microbes in compost into water and apply the soluble compost extract by spraying. This is basically the only feasible method of applying this nutrient to growing fields. Solubilized compost sprayed directly onto plants can also have pesticidal activity which is attributed to the microbial content, thus eliminating or diminishing the need for commercial pesticides. Compost extract can be fortified with other nutrients or microbes ("compost tea"), or diluted according to the requirements of the target crop. In some applications, methods for measuring the microbial content of soils can be used to determine the optimal concentration of solubilized compost for application to target crops. For example, solubilized composts can be diluted or concentrated from several billion parts/ml up to a million parts/mL, or less than a million parts per mL, based upon the microbial content of the sample. The concentration of microbes can be used to determine the dilution factor that should be used for spraying of the extract or tea. It is also useful for evaluating compost extract conditions for optimal microbial content and nutritional additives used to increase microbial population of a compost extract.

2. Soil Microbes

Microbial life within the soil is a key factor in enhancing plant growth. Typically, the microbial biomass of a soil correlates with the ability of a soil to support the growth of plants. Soil microbes play an important role in the physical and chemical formation of soils. Soil microbes exude a glue that allows them to cling to soil particles and which also gives the clumpy structure to soil. This clumpy structure is a critical component of soil health as it retards erosion, provides aeration, and increases water holding capacity of the soil. Microbes convert soil nutrients into forms that can be used by plants, control pathogens and bind the soil making it capable of retaining water and air. Thus, the microbial food chain in soil has been linked to crop yield and the presence of microbes within soil can be used as a marker for soil quality and fertility. At the bottom of the food chain are bacteria that provide food for protozoa like paramecia and amoeba, which are in turn grazed upon by nematodes that then feed larger animals such as earth worms and insects. In this process of grazing on bacteria which are rich in organic nitrogen, ammonia and nitrates are released for use by plants Bacteria are single-celled prokaryotic organisms, typically 1-8 micrometers in length. One gram of healthy soil typically contains $10^6$ to $10^8$ bacteria. The number of species of bacteria per gram of soil has been estimated as between 2000 and 8.3 million (Gans, et al., Science, 309:1387-1390 (2005); Schloss and Handelsman, *PLoS Comput Biol.*, 2(7): e92. (2006)). The most abundant bacterial groups in soil samples from the Western Hemisphere were the Bacteroidetes, Betaproteobacteria and Alphaproteobacteria (Roesch, et al., *ISME J.*, 1:283-290 (2007)). Exemplary soil bacteria include *Nitrosomonas* spp., *Nitrobacter* spp., *Rhizobium* spp., *Bradyrrhizobium* spp., *Azotobacter* spp, *Bacillus* spp., *Azotobacter* spp., *Micrococcus* spp., *Achromobacter* spp., *Nitrosococcus* spp., *Pseudomonas* spp., *Serratia* spp., *Xanthomonas* spp. and *Clostridium*, spp.

Bacteria are responsible for biochemical transformations within soil and directly or indirectly provide nutrients for plant life. In return up to 30-50% of the nutrition the plant sends to the root is released into the soil to support local microbial communities. This relationship is reciprocal: the plant feeds the microbes, the microbes, as they die, feed the plant. It has now been demonstrated that the microbial biomass in the plant area is a critical indicator of the plant/health/metabolism: soil around roots of plants that are dying or going to seed have dramatically lower microbial load than their healthy counterparts. As a plant is fertilized, the microbial biomass increases as do other critical indices of plant health.

Important biochemical processes carried out by soil bacteria include ammonification (i.e., protein to ammonia), nitrification (i.e., ammonia to nitrites, to nitrates), denitrification (i.e., release of free elemental nitrogen) decomposition of cellulose and other carbohydrates, the symbiotic and non-symbiotic fixation of atmospheric nitrogen, as well as the oxidation and reduction of iron and sulfur compounds.

Bacteria also contribute to compost fertility by preventing pathogens through the production of bacteriocins and antibiotics, as well as by competition.

Other microorganisms present in the soil sample include actinomycetes, fungi, algae, and protozoa. The soil microorganisms are discussed extensively by Sylvia et al. "Principles and Applications of Soil Microbiology." Upper Saddle River: Prentice Hall, New Jersey, (1998).

Actinomycetes are a type of bacteria, but they share some characteristics with fungi that are most likely a result of convergent evolution due to a common habitat and lifestyle. Fungi are abundant in soil, but bacteria are more abundant. Fungi are important in the soil because of their beneficial symbiotic relationships with plants, as primary degraders of raw cellulosic material, as inhibitors of pathogens and as food sources for other, larger organisms. Soil fungi can be split into two groups based on their relationship to plants. Mycorrhiza are fungi that are intimately connected to and dependent upon the plant for their survival. Mycorrhiza increase the root area of a plant and are critical to the plant's access to water and mineral nutrients. The non-mycorrhizal fungi function to break down cellulosic materials, making the degradation products available to bacteria. These are most active when there is an abundance of material for digestion. Fungi are classified into species based primarily on the size, shape and color of their reproductive spores, which are used to reproduce, Most of the environmental factors that influence the growth and distribution of bacteria and actinomycetes also influence fungi. The quality as well as quantity of organic matter in the soil has a direct correlation to the growth of fungi, because most fungi consume organic matter for nutrition. Fungi thrive in acidic environments, while bacteria and actinomycetes cannot survive in acid, which results in an abundance of fungi in acidic areas. Fungi also grows well in dry, arid soils because fungi are aerobic, or dependent on oxygen, and the higher the moisture content in the soil, the less oxygen is present for them.

Algae can be split up into three main groups: the Cyanophyceae, the Chlorophyceae and the Bacillariaceae. The Cyanophyceae contain chlorophyll, which is the molecule that absorbs sunlight and uses that energy to make carbohydrates from carbon dioxide and water and also pigments that make it blue-green to violet in color. The Chlorophyceae usually only have chlorophyll in it which makes it green, and the Bacillariaceae contain chlorophyll as well as pigments that make the algae brown in color.

Protozoa are eukaryotic organisms that were some of the first microorganisms to reproduce sexually, a significant evolutionary step from duplication of spores, like those that many other soil microorganisms depend on. Protozoa can be split up into three categories: flagellates, amoebae and ciliates.

3. Obtaining Samples

Samples of solid soil can be collected and measured in the field using a soil collection device and/or measuring cup or a 3 ml syringe modified for use as a punch with plunger which allows measurement of soil volume by the gradations on the syringe, and direct insertion of sample into the reaction vial. For example, multiple samples of equal volume are taken across a certain area and combined in a clean mixing vessel to produce a composite sample. In other aspects, a sample is obtained by inserting a collection device into a batch of solid compost or soil. Sieving through a 2-5 mm sieve may be required to remove roots and rocks and other solid material that could adversely affect the integrity of the sample and impact results.

Solid soil samples can be measured using a collection vessel of a known volume. In one embodiment, solid soil is packed into a measuring vessel, such as a cup washer, to a volume of 0.210 ml. Alternatively, a punch with a plunger and a defined volume can be used to deliver between 0.2 and 1 cc of sample. Measurement of sample by volume corrects for soil water content. The volume of the cup washer is 0.21 ml, i.e., it holds 210 microliters of water. As can be seen in Table 1, a soil sample can hold more than 2× dry weight of soil before volume changes.

TABLE 1

Soil Volume as Function of Water Content

| μls water added | Weight Sample 1 | Weight Sample 2 | |
|---|---|---|---|
| 0 | 0.98 | 0.132 | |
| 25 | 0.103 | 0.155 | |
| 25 | 0.124 | 0.177 | |
| 25 | 0.146 | 0.201 | |
| 25 | 0.172 | 0.223 | |
| 25 | 0.197 | 0.257 | water seeped out bottom |
| | 0.2197 | | |
| | 0.24 | | water seeped out bottom |

Measuring volume compensates for water content of sample. The sample can hold more than 2× dry weight of soil before volume changes.

Solid and liquid samples are placed into a clean reaction vial. Solid samples that have been measured in a measuring cup can be transferred into the vial within the cup. Samples taken by punch can be directly delivered into the reaction vial by depressing the plunger. Liquid samples that have been measured using a pipette or the cap of the reaction vial can be introduced into the vial by removing 2 ml from the vial and measuring 2 ml of the compost extract into the vial.

B. Release of Soil Microbes into Extraction Fluid

Release of microbes from the soil sample into the extraction fluid occurs due to the action of releasing agents as well as due to mechanical agitation of the soil sample in the extraction fluid.

Soil samples are solubilized within the reaction vial by addition of water and/or an extraction fluid, followed by physical agitation to release soil-associated microbes into solution. The extraction fluid contains releasing agents, and may optionally contain clarification agents, preservatives, and/or anti-foaming agents. The amount of releasing agent, preservative, clarification agent or anti-foaming agent added to a soil sample can vary depending on the nature of the soil sample and the desired results. 10 ml of extraction fluid is capable of releasing ½ to 2 ml of soil or 1-4 ml of compost extract.

1. Releasing Agents

Releasing agents enable or enhance the solubilization of microbes within a soil sample by increasing dissociation of the microbes from soil particles. Releasing agents should not cause extensive foaming of the solution. Releasing agents for use in the methods are non-toxic and do not affect the visualization or measurement of microbes within the time required for analysis or for up to several hours afterward. In addition, releasing agents may be stable for extended periods of time and can be packaged and stored in a ready-to-use form. Releasing agents can be provided in premeasured ready-to-use form or packaged as a tablet or powder that when added to a set volume of water produce an extraction fluid. Tablets may alleviate the requirement for preservatives and the restrictions on transport of fluid. Tablets/powder must provide reagents that can be solubilized within the whisking time.

Extraction of microbes is very sensitive to the following variables: the concentration of salts and detergent, the time of whisking and the settling time In a preferred embodiment, the assay is optimized to allow the least variation in extraction with variation of the variables. For example, the least variation in number of microbes extracted is seen with TWEEN® concentrations between 0.35 and 0.42% TWEEN®®.

While few microbes can survive the high salt concentration of the extraction fluid, microbial contamination can cause a decrease in TWEEN® concentration which seriously compromises assay efficacy: TWEEN® 20 is sensitive to decomposition by microbial contamination. Sodium azide at concentrations from 0.02 to 0.1% was shown to provide stability to the TWEEN® concentration. See FIGS. 2A-2C, discussed below in the examples.

Typically, the releasing agents include inorganic salts and detergents. For example, the releasing agents can include NaCl, KCl, $CaCl_2$, $MgCl_2$, and detergents, such as a polysorbate-type nonionic surfactant like TWEEN® 20. In a preferred embodiment, the extraction fluid contains between about 0.3 and 10% NaCl, between about 3-5% CaCl, and between about 0.01% to 0.5% of a polysorbate-type nonionic surfactant In the most preferred embodiment, the extraction fluid for extracting microbes up to 100 μm in size is 10% NaCl, 2.2% CaCl2, 0.4% TWEEN® 20 and 0.1% sodium azide.

Total microbial biomass does not always correlate well with the bacterial microbial biomass. In samples of compost there are typically very few protozoa, thus the method does not show the ~2 fold increase that is seen with soil. In soil, a relatively constant ratio of bacteria to protozoal predators is generally observed. Microscopic examination of the extraction fluid shows that protozoa, especially amoeba and fungal spores, are highly colored organisms.

Soils in winter tested the same week after week and samples of these soils that maintained moisture and were kept at room temperature ("RT", approximately 25° C.) or refrigerated (4° C.) tested stably over months. It is hypothesized that these dormant organisms are in a stable state. However, once plants began to grow, a dramatic downward fluctuations in the number of microbes was observed once they are removed from the soil habitat. A growing plant nourishes the microbial population around it by exuding sugars and peptides, which stimulates bacterial growth, which feed protozoa, which in turn multiply and feed the organisms that feed on protozoa. It would appear that actively multiplying microbes are much more sensitive to their environment and their deaths are the cause of the 50% or more decline in microbial biomass that was observed over one to three days at room temperatures during the growing season. This highlights an intrinsic advantage of an on-site test such as the one described herein. During the growing season, the only real picture of the microbial biomass is that seen under the growth conditions which favors on site testing.

Mild detergent releasing agents are preferred. Exemplary detergents include blends of polyether-polymethylsiloxane-copolymer and nonionic surfactant, or polyether modified polysiloxane (CAPSIL®), TWEEN®® 20, TWEEN®® 80, also referred to as polysorbate 20 or 80, dioctanoylphosphatidyl choline and polyethylene-polypropylene glycol. In one embodiment, the releasing agent is either 0.1% TWEEN®® 20 or CAPSIL®. CAPSIL® can be a liquid at a 0.1%, 1%, 10%, 50% or 100% formulation in a dispensing vial. A particular test concentration of CAPSIL® is 0.2%.

The reagents may be provided in preformed premeasured liquid form, or in premeasured tablet or powder form ready to be diluted with predetermined volume of water.

2. Clarifying Agents

Clarifying agents are disclosed. Solubilized soil samples containing humic acid can be dark brown in color. Unless it is a very high concentration, humic acid and other pigments do not affect the quantitative measurement of microbes on the membrane because humic acid does not bind to the fiberglass membrane and is too small to be retained on the surface of the membrane. Should a pigment be present in sufficient quantity to color the entire membrane, it should color the quality control window and alert the tester to the interference. It should be possible to subtract the intensity of the quality control window from the intensity of the sample window.

Clarifying agents may neutralize the pigmentation of soluble soil samples to facilitate accurate measurements of turbidity, reflectance and/or transmittance. Preferred clarifying agents for use in the methods do not affect the visualization or measurement of microbes within the time required for analysis or for several hours afterward. Exemplary clarifying agents in some conditions include hydrogen peroxide, chlorine dioxide, or mixtures of sodium hypochlorite, sodium chloride, sodium carbonate, sodium hydroxide and sodium polyacrylate (i.e., CLOROX® Regular Bleach). Numerous clarifying agents are commercially available. Typically, clarifying agents do not cause any damage to microbes in the time it requires to perform the methods and measurements of the test.

3. Anti-Foaming Agents

Anti-foaming agents or "defoamers" are also disclosed. Anti-foaming agents act by decreasing the surface tension of gas bubbles and reducing foam. Exemplary anti-foaming agents include alcohols, stearates, insoluble oils, polydimethylsiloxanes, other silicones and glycols. Anti-foaming agents can prevent the formation of foam or can be added to disperse a foam that has formed. Anti-foaming agents can be added as a measured amount of dry powder, or as a tablet. One example of an anti-foaming agent is poly(dimethylsiloxane), the silicon dioxide simethicone. An exemplary concentration of simethicone is 125 milligrams of simethicone in a volume of 25 mL or 5 milligrams per mL solution. For example, an anti-foaming agent is present, such as CAPSIL®.

In one embodiment, a clarifying agent is added to a final concentration of about 50-150 ppm or final CLOROX® concentration of 10%.

A releasing agent such as CAPSIL® may also be added to the soil sample in the reaction vial. For example, CAPSIL® may be added to a final concentration of 0.2%. CAPSIL® is a 100% active blend of organo-silicone and non-ionic surfactants that enables solutions to spread, sold by Aquatrols, NJ. CAPSIL® is not stable when diluted in clarifying reagent but 0.1% TWEEN®® gives the same result and is stable in the diluted reagent.

For example, a single tablet of a clarification agent and a single, measured drop of releasing agent are added to 200 ml-400 ml of solid soil or 2 mL of compost extract in the reaction vial immediately prior to the addition of water and shaking. Alternatively, 5×50 μl drops of a saturated solution of Chlorine Dioxide and a 20 μl single drop of CAPSIL® are added to 200-400 ml of solid soil or 1-2 mL of liquid soil in the reaction vial immediately prior to the addition of 10 ml water and shaking. 10 mL of a premixed solution of clarifying and releasing agent consisting of 0.08 mg/mL Chlorine Dioxide and 0.1% TWEEN®® 20 may be provided in the reaction vial.

Anti-foaming agents can be used to prevent or reduce the formation of bubbles resulting from agitation. Anti-foaming agents such as the silicon dioxide simethicone can be added according to the requirements of the sample. For example, simethicone is added to a final concentration of 5 milligrams per ml. Anti-foaming agents can be added prior to shaking to prevent formation of foam, or can be added after shaking to disperse foam that has formed, according to the requirements of the sample.

The mixture of soil samples including releasing agents, clarification agents and/or anti-foaming agents are solubilized by the addition of tap water to the reaction vial. For example, water is added to the reaction vial to a total volume of 10 mL. Water can also be added to a total volume of less than 10 mL, such as to make a total volume of 1 mL, 2 mL, 3 mL, 4 mL, 5 mL, 6 mL, 7 mL, 8 mL or 9 mL, according to the requirements of the operator. Sufficient water can also be added to a final volume of more than 10 mL, such as to up to 25 mL, or more than 25 mL.

Immediately following the addition of water, the reaction vial cap is screwed onto the vial and the contents are mixed by vigorous agitation. Agitation can be manual (i.e., shaking by hand, for example, in a vertical and/or horizontal plane), or can be assisted by the use of an automated agitation device, such as a vortex shaker ("vortexing"), sonication or a device similar to a ROBART® Shaker device or by a vibrating probe.

The amount of agitation required to dissociate microbes from soil particles can vary depending upon the nature and quantity of the sample and depending upon the method of shaking. Vigorous shaking by hand for 10 to 20 minutes can be sufficient to release microbes from 200-400 ml of solid soil or 2 mL of liquid soil into 10 ml of solution in the absence of releasing agent. In the presence of a releasing agent such as 0.2% CAPSIL® 5-20 minutes of agitation by hand shaking or 1 minute of agitation using a ROBART® shaker, or 10-20 seconds of a vibrating probe should be sufficient to release the microbes from 0.2-0.5 ml of solid soil or 1-2 mL of liquid soil.

Immediately following agitation, the vial is placed vertically in a rack with the cap facing upwards. The cap is removed from the reaction vial and the solution is allowed to settle for 10-30 seconds, or up to 10 min.

4. Reaction Vials

Soil samples for use with the methods and devices are solubilized within a reaction vessel or vial. For example, the tube has a diameter of 17 millimeters and a length of 120 millimeters and holds a volume of 15 mL. In other forms, the tube is sized to contain a volume of more than 15 mL, such as 50 mL, or more than 200 mL. An exemplary reaction vial is a polypropylene screw-cap vial, such as a conical centrifuge tube (e.g., Corning Life Sciences product No.: 352097). In some forms, the cap of the vial is threaded to seal the entire circumference of the vial. The cap of the reaction vial can hold a volume of 1 or 2 mL, or more than 2 mL when completely filled. In a particular form, the reaction vial is made of a hydrophobic material with an inert inner surface and the reaction vial is transparent to facilitate visual inspection of the contents. The outer face of the vial can contain graduated marks to enable visual estimation of the volume of fluid within the vial. The reaction vial should be clean and free from microbial contaminants.

C. Agitation Devices

Devices for mixing soil solutions by agitation or shaking are commercially available from multiple sources. Commercially available portable battery-operated shakers, such as the "Robart shaker" are useful in the field. The battery operated version of the Robart shaker is small and incorporates easily into a portable field kit. Other commercially available shakers, such as those suitable for shaking small paint or nail polish samples can also be used. Electrically powered laboratory equipment for mixing fluids, such as the Vortex mixer, and ultrasonic equipment such as sonicators are useful in the laboratory setting. A preferred device is a milk frother with the tip removed and replaced by a plastic tube coating the wand so that the wand reaches the bottom of the reaction vial—usually a requirement to ensure that the total volume of soil added to the reaction vial is whisked. Another method is to use of a battery operated vibrating wand, such as can be constructed using an ORAL® B children's tooth brush base with a plastic straw attached for penetrating the reaction vial.

D. Measuring the Microbial Load

The membrane should be selected so that it is not stained by soil pigments and does not bind other particles than the microbes of up to 200 micrometers present in the extraction fluid.

Microbial biomass is estimated by spectrophotometric assay of the extracted solution or by the membrane method. If estimated by the membrane method it can be analyzed visually or by cell phone grey scale app. The test is read by comparing the intensity of the sample site to a gray scale which allows one compensate for the various pigments in different soils (yellow, red, gray brown): using a gray scale through a red (or other) filter allows one to detect color intensity not color itself. Analysis of the pigmented intensity by grey scale, compensates for the various pigments. The red filter can be a photographic quality clear red sheet applied to the label or one can use a gray scale with red lens glasses. It is also possible to use other colored filters. By cell phone app only the white pixels are measured ensuring that pigment hue does not influence the analysis.

The MicroBiometer™ gray scale reflects 6 soil ratings, very poor, poor, acceptable, good, very good, and excellent. These ratings have been assigned based on correlation of this method with PLFA. See Fig XX showing correlation of this method with PLFA The gray scale may not only be in the form of color strips. The gray scale strips may be in any form: chart, strip, color discs, or have digital values for the color shades to aid with electronically establishing the soil microbial load. Electronic forms of the gray scale colorimeter may be provided as smart phone applications. The electronic form of the gray scale colorimeter may read the intensity of the membrane strip at the sample window using the end user's cell phone and estimate microbial biomass using a curve.

After the sample has been analyzed using the MicroBiometer™ gray scale strips, it is possible to analyze the same extraction fluid using a filter tube and get a colorimeter reading (as per Old Assay). Another advantage of the new assay is that the flotsam and jetsam that often floats on the top of the extraction fluid does not interfere in the membrane assay: It is usually too large to be picked up by the pipettor and/or as it is large can be brushed off the membrane surface.

Overall, the microbial load detection method described herein uses an extraction fluid, does not require filtration, and can be read out on a membrane. This test can be performed using the MicroBiometer™ Strip test.

V. Kits

Kits including a device with or separately from a plurality of membranes, optionally with one or more of a whisking device, containers, sampling devices, pipettes, and the gray scale colorimetric strips for single or repeat measurements are provided. Sample measuring devices such as cups, lids, spoons, boats, or straws can be provided. Optionally, the kits may also include sample whisking devices. Kits are provided with instructions for measuring the microbial load of the soil.

Kits may be provided to include a plurality of membranes, packages, and the gray scale colorimetric strips and a measuring cup with a capacity of 0.2-1 cc of soil when fully packed, or a 3 ml syringe modified for use as a punch with plunger which allows measurement of soil volume by the gradations on the syringe, and direct insertion into the reaction vial, a vial containing detergent/releasing agent, an anti-foaming agent, a bleaching agent tablet, a reaction vial, and a pipette for drawing out an extraction fluid containing the suspended microorganisms, may be provided. For example, the kits may also contain a portable automated shaker device whisker, such as the small Robart shaker or a battery operated vibrating wand, such as can be constructed using milk frother adapted with a plastic probe attached for penetrating the reaction vial. In a preferred embodiment the whisker is manufactured without the frothing tip and has a timer that limits whisking to the optimum whisking time, e.g. thirty seconds.

The present invention will be further understood by reference to the following non-limiting examples.

EXAMPLES

Example 1. Microbiometer™ with Gray Scale

Materials and Methods

The methods of using the device, such as the MicroBiometer™ Strips, requires suspending a measured volume of soil or compost in extraction fluid, whisking at a controlled vigor and time to separate the microbes from the soil, allowing the soil particles to settle for a short time, for example, 10 minutes, and then quantitating the microbes suspended in the top 5 ml of solution by colorimetric instrument or via a strip assay.

An extraction sample requires filtration if it is to be read by absorbance. The sample usually does not require filtration before a strip assay. However, compost samples, because of debris, may require filtration, and can be read colorimetrically using grey scale on a membrane or spectrophotometrically.

The devices are shown in FIGS. 1A and 1B. A typical card contains 10 to 12 test windows 12, 22. The grey scale 14 is shown under the sample windows 12 in FIG. 1A. A red rectangle 24 is placed over the bottom middle sample 36 of the device 30 and the corresponding sample concentration indicated.

Example 2: Determination of Most Effective Extraction Fluid

Materials and Methods

Fresh soils were tested. ½ cc of soil was added to extraction fluid at 2% NaCl, 3.2% CaCl and 0.1% TWEEN® 20, or extraction fluid at 10% NaCl, 2.2% CaCl, 0.4% TWEEN®. All samples were whisked for 30 seconds using an adapted milk frother and then allowed to settle for 10 minutes before inserting serum separator as filter and reading A430 converting to mg/ug by curve.

The effect of extraction fluid concentration: 1×, 0.8×, 0.6×, and 0.4×9.2% NaCl 3.4% CaCl with 0.35% Tween 200.35% Tween 20 on soil extraction efficiency was determined based on absorbance at 430 nm.

The effect on soil extraction as a function of % Tween 20 concentration: 0.2, 0.4, 0.6 and 0.8 on soil extraction efficiency was also assessed.

The correlation of soil extraction efficiency in the range of 0.01% to 0.375% Tween 20 was measured and calculated.

Results

Figure 2A:
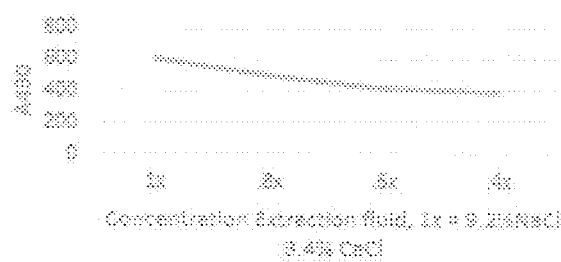
FIG. 2A shows the correlation between extraction fluid concentration (1×, 0.8×, 0.6×, and 0.4×9.2% NaCl 3.4% CaCl with 0.35% Tween 200.35% Tween 20) and soil extraction efficiency (absorbance at 430 nm).
Figure 2B:
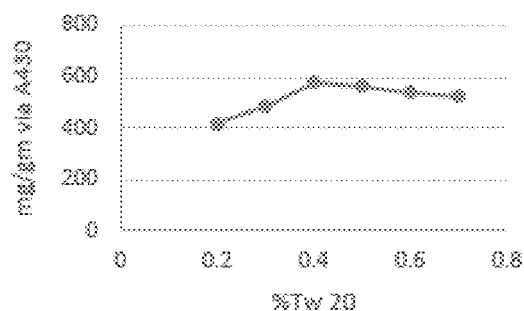
FIG. 2B is the effect on soil extraction as a function of % Tween 20: 0.2, 0.4, 0.6 and 0.8.
Figure 2C:
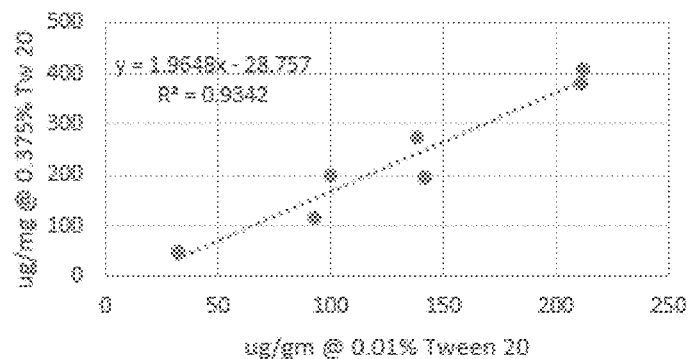
FIG. 2C is a graph of the correlation of soil extraction efficiency in the range of 0.01% to 0.375% Tween 20.

FIG. 2A shows the correlation between extraction fluid concentration (1×, 0.8×, 0.6×, and 0.4×9.2% NaCl 3.4% CaCl with 0.35% Tween 200.35% Tween 20) and soil extraction efficiency (absorbance at 430 nm). FIG. 2B is the effect on soil extraction as a function of % Tween 20: 0.2, 0.4, 0.6 and 0.8. FIG. 2C is a graph of the correlation of soil extraction efficiency in the range of 0.01% to 0.375% Tween 20.

The results demonstrate that good results were obtained under all conditions.

Based on these results, the preferred extraction fluid is 10% NaCl, 3.2% $CaCl_2$, 0.4% TWEEN®.

Example 3: Calculation of Dose Response Curve

Methods and Materials

The same device and reagents were used as determined in Examples 1 and 2.

Soil sample extractions were tested by applying one drop to the first well, then 2, 3, 4, 5, 6, 8, 10, 12 and 16 drops.

A test sample was assayed on the membrane by applying 1 to 16 drops. The intensity was read on the grey scale as follows: samples that matched the level perfectly were rated a whole number. Samples whose intensity fell midway between 2 levels were assigned the number+0.5. Samples that were slightly darker or lighter than the grey scale they most matched were assigned +0.02 or −0.2.

Results

Figure 3:
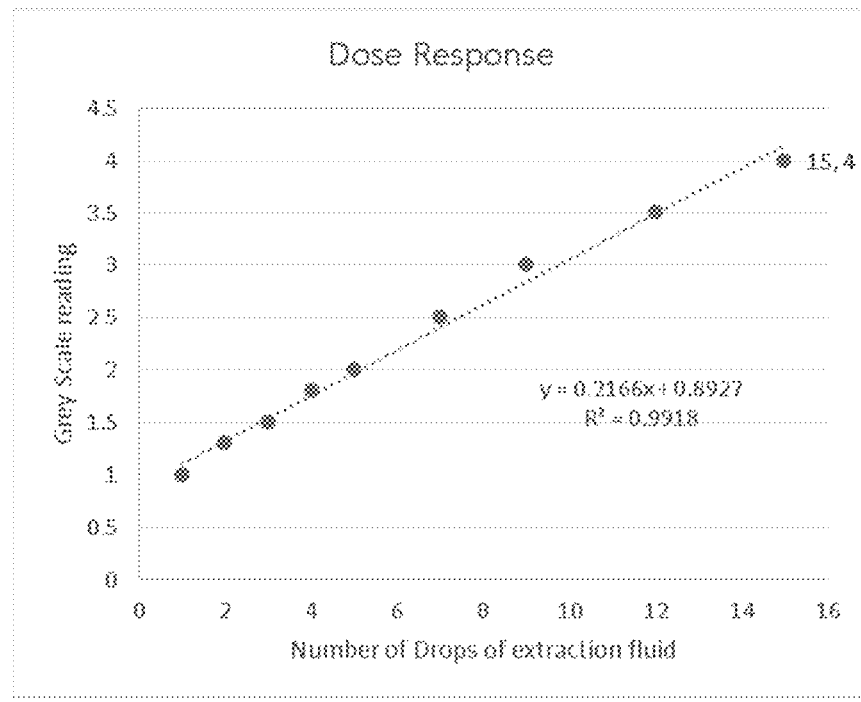
FIG. 3 is a graph illustrating the dose response seen when a sample is read on the grey scale. A test sample was assayed on the membrane by applying 1 to 16 drops. The intensity was read on the grey scale as follows: samples that matched the level perfectly were rated a whole number. Samples whose intensity fell midway between 2 levels was assigned the number+0.5. Samples that were slightly darker or lighter than the grey scale they most matched were assigned+0.02 or −0.2.

FIG. 3 is a graph illustrating the dose response seen when a sample is read on the grey scale.

Example 4: Accuracy of Test on Dead Versus Alive Microorganisms

Materials and Methods

The methods and devices were the same as used in the earlier examples.

Phospholipid Fatty Acid analysis (PLFA) was run on fresh in house samples of soil and compost. PLFA is run on samples that have been frozen and thawed. Freeze thaw is a technique used to disrupt microbes.

Results

Figure 4:
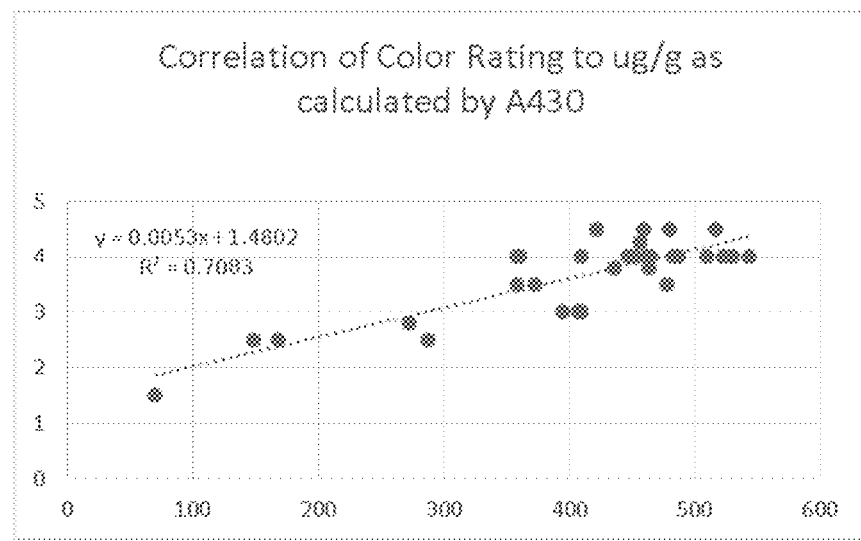
FIG. 4 is a graph of the correlation of assay with Phospholipid Fatty Acid analysis (PLFA). The assay was run on fresh in house samples of soil and compost. PLFA is run on samples that have been frozen and thawed. Freeze thaw is a technique used to disrupt microbes. This probably does not affect the assay for PLFA but it dramatically affects the assay which detects intact microbes only. Accordingly the data correlates the assay on fresh soil with PLFA results. The assay and PLFA did not correlate when assaying raw compost samples. Raw compost is a soil material in rapid flux.

As shown by FIG. 4, this probably does not affect the assay for PLFA but it dramatically affects the assay which detects intact microbes only. Accordingly the data correlates the assay on fresh soil with PLFA results. The assay and PLFA did not correlate when assaying raw compost samples. Raw compost is a soil material in rapid flux.

Example 5: Correlation of Color Rating to µg/g as Calculated by Absorbance

Materials and Methods

The same materials, devices and methods were used as described in the foregoing examples.

Sample extracts were measured by absorbance on a spectrophotometer at 430 nm, and by comparison on color on test strip to color scale.

Results

FIG. 4 is a graph showing the correlation of grey scale reading to the estimate of µg/gm microbial biomass when sample is assayed at A430 and analyzed by curve. R2 of 0.7 is very common when comparing methods of estimating microbial biomass and is considered very adequate in the literature Example 6: Effect of Whisking Time on Results Materials and Methods Materials, devices and methods were the same as described above.

Fresh as well as dried samples were tested and results measured by absorbance using a spectrophotometer at 430 nm.

Samples were tested after whisking for 15, 30, and 60 seconds. Dry samples were also tested after whisking for 180 and 300 seconds.

Results

Figure 5:
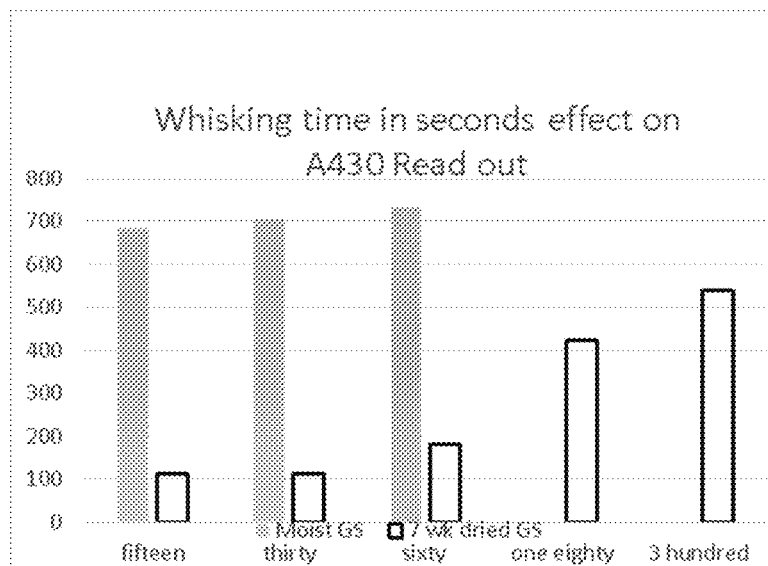
FIG. 5 is a graph showing the correlation of grey scale reading to the estimate of ug/gm microbial biomass when sample is assayed at A430 and analyzed by curve. R2 of 0.7 is very common when comparing methods of estimating microbial biomass and is considered very adequate in the literature

FIG. 5 shows the effect of whisking time on the amount of microbial biomass (y axis). Fresh samples, solid bars show only slight increases in release following 15 second whisking. Dried sample (open bar) continues to release microbes for up to and beyond 3 minutes of whisking.

Modifications and variations of the present invention will be understood by those skilled in the art and are intended to come within the scope of the appended claims.

I claim:

1. A device for measuring total microbial content of a soil sample dispersed in an extraction fluid comprising
   a substrate having a plurality of sample application sites thereon,
   each sample application site comprising a fluid-absorbable membrane, optionally including a sample window and/or a quality control window,
   wherein the fluid-absorbable membrane is wettable by the sample within about 5 seconds to 30 seconds of applying the sample, and
   wherein the fluid-absorbable membrane retains the soil sample microbes having a size of between about 1 micrometer and 200 micrometers on the surface but not pigments in the soil sample.

2. The device of claim 1, wherein the fluid-absorbable membrane is secured between two adhesive-coated sheets so that there is a sample application site on one side of the membrane.

3. The device of claim 2, further comprising a quality control application site.

4. The device of claim 1, wherein the device has a depth of between about 0.1 mm and 10 mm.

5. The device of claim 1 wherein the application site can absorb a volume of between 100 μl and 1 ml.

6. The device of claim 1, wherein the fluid-absorbable membrane is formed of a polymer selected from the group consisting of anopore (ANP), cellulose acetate (CA), cellulose nitrate (CN), nylon/polyamide (NYL), polycarbonate (PC), polyethersulfone (PES), polypropylene (PP), regenerated cellulose (RC), and fiberglass.

7. The device of claim 1 further comprising one or more color scales on the same side of the device as the sample application sites.

8. The device of claim 7 wherein the color scales are adjacent to the application sites.

9. A method of measuring the microbial load of a soil comprising applying an extracted soil sample to a device for measuring total microbial content of a soil sample dispersed in an extraction fluid comprising
   a substrate having a plurality of sample application sites thereon,
   each sample application site comprising a fluid-absorbable membrane, optionally including a sample window and/or a quality control window,
   wherein the fluid-absorbable membrane is wettable by the sample within about 5 seconds to 30 seconds of applying the sample, and
   wherein the fluid-absorbable membrane retains the soil sample microbes having a size of between about 1 micrometer and 200 micrometers on the surface but not pigments in the soil sample, and
   detecting the microbial load with a color scale.

10. The method of claim 9, wherein the fluid-absorbable membrane is secured between two adhesive-coated sheets so that there is a sample application site on one side of the membrane.

11. The method of claim 9, further comprising a quality control application site, the method comprising applying a control standard to the control application site.

12. The method of claim 9, wherein the device has a depth of between about 0.1 mm and 10 mm.

13. The method of claim 9 wherein the application site can absorb a volume of between 100 μl and 1 ml, comprising applying a sample volume of between 100 μl and 1 ml.

14. The method of claim 9, wherein the fluid-absorbable membrane is formed of a polymer selected from the group consisting of anopore (ANP), cellulose acetate (CA), cellulose nitrate (CN), nylon/polyamide (NYL), polycarbonate (PC), polyethersulfone (PES), polypropylene (PP), regenerated cellulose (RC), and fiberglass.

15. The method of claim 9 further comprising one or more color scales on the same side of the device as the sample application sites, the method comprising comparing the color at the sample application site with the color scale.

16. The method of claim 15 wherein the color scales are adjacent to the application sites.

17. The method of claim 9 further comprising:
   obtaining a soil sample containing microorganisms;
   extracting the pigments from the soil sample by mixing an extraction fluid with the soil sample sufficiently to extract the microorganisms into the extraction fluid;
   allowing the extracted soil sample to settle;
      applying the extracted soil sample onto a device for measuring total microbial content of a soil sample dispersed in an extraction fluid comprising
   a substrate having a plurality of sample application sites thereon,
   each sample application site comprising a fluid-absorbable membrane, optionally including a sample window and/or a quality control window,
   wherein the fluid-absorbable membrane is wettable by the sample within about 5 seconds to 30 seconds of applying the sample, and
   wherein the fluid-absorbable membrane retains the soil sample microbes having a size of between about 1 micrometer and 200 micrometers on the surface but not pigments in the soil sample;
   allowing color to develop on the device;
   obtaining the microbial load by comparing the shade of the developed color with colors present on the color scale.

18. The method of claim 17, wherein the color scale represents at least six soil ratings: very poor, poor, acceptable, good, very good, excellent.

19. The method of claim 9, wherein the fluid-absorbable membrane of the device is dipped in the soil sample extract.

20. The method of claim 9, wherein the extraction fluid comprises releasing agents sodium chloride, calcium chloride, and a polysorbate-type nonionic surfactant.

21. The method of claim 20 wherein the extraction fluid contains between about 0.3 and 10% NaCl, between about 3-5% CaCl, and between about 0.01% to 0.5% of a polysorbate-type nonionic surfactant.

22. The method of claim 21 wherein the extraction fluid is 10% NaCl, 3.2% $CaCl_2$, and 0.4% a polysorbate-type nonionic surfactant.

23. A kit comprising
   a device for measuring total microbial content of a soil sample dispersed in an extraction fluid comprising
   a substrate having a plurality of sample application sites thereon,
   each sample application site comprising a fluid-absorbable membrane, optionally including a sample window and/or a quality control window,
   wherein the fluid-absorbable membrane is wettable by the sample within about 5 seconds to 30 seconds of applying the sample, and wherein the fluid-absorbable membrane retains the soil sample microbes having a size of between about 1 micrometer and 200 micrometers on the surface but not pigments in the soil sample,
and at least one of the following:
instructions for use,
sample applicator,
extraction fluid,
whisking device, or
color scale,
for use in a method of measuring the microbial load of a soil comprising applying an extracted soil sample to a device for measuring total microbial content of a soil sample dispersed in an extraction fluid comprising
a substrate having a plurality of sample application sites thereon,
each sample application site comprising a fluid-absorbable membrane, optionally including a sample window and/or a quality control window,
wherein the fluid-absorbable membrane is wettable by the sample within about 5 seconds to 30 seconds of applying the sample, and
wherein the fluid-absorbable membrane retains the soil sample microbes having a size of between about 1 micrometer and 200 micrometers on the surface but not pigments in the soil sample, and
detecting the microbial load with a color scale, wherein the fluid-absorbable membrane is secured between two adhesive-coated sheets so that there is a sample application site on one side of the membrane.

24. The kit of claim 23, further comprising premeasured releasing agents, an anti-foaming agent, a bleaching agent tablet, a reaction vial, and a pipette for drawing out an extraction fluid containing suspended microorganisms.

* * * * *